United States Patent [19]

Braun et al.

[11] 4,024,393
[45] May 17, 1977

[54] APPARATUS FOR ANALYZING FREE-FLOWING MATERIAL

[75] Inventors: Hartmut Braun, Karlsruhe; Fritz Riffel, Graben-Neudorf; Walter Hartung, Ludwigshafen, all of Germany

[73] Assignee: Gesellschaft fur Kernforschung m.b.H., Karlsruhe, Germany

[22] Filed: Mar. 29, 1976

[21] Appl. No.: 671,371

[30] Foreign Application Priority Data
Mar. 29, 1975 Germany .......................... 2514062
Apr. 12, 1975 Germany .......................... 2515981

[52] U.S. Cl. .............................. 250/303; 250/390
[51] Int. Cl.² ...................... G01T 1/161; G01T 3/00
[58] Field of Search .......... 222/368, 362; 250/303, 250/306, 308, 363, 364, 436, 432, 499, 255

[56] References Cited

UNITED STATES PATENTS

| 3,213,280 | 10/1965 | Burley | 250/390 |
| 3,245,590 | 4/1966 | Hawkins | 222/368 |
| 3,600,574 | 8/1971 | Glaza | 250/390 |
| 3,781,556 | 12/1973 | Taylor et al. | 250/303 |

Primary Examiner—Harold A. Dixon
Attorney, Agent, or Firm—Spencer & Kaye

[57] ABSTRACT

An apparatus for analyzing flowable material in intermittent sequence comprises a hollow dosing sphere having a predetermined inner volume for forming samples of constant volume of the material introduced thereinto; a hollow radiation sphere connected to the outlet of the hollow dosing sphere; a radiation source supported within and centrally with respect to the hollow radiation sphere for a homogeneous activation of the sample introduced thereinto from the hollow dosing sphere; a hollow measuring sphere connected to the outlet of the hollow radiation sphere; and a detector arranged in the hollow measuring sphere for sensing the activity of the irradiated sample introduced thereinto from the hollow radiation sphere.

12 Claims, 2 Drawing Figures

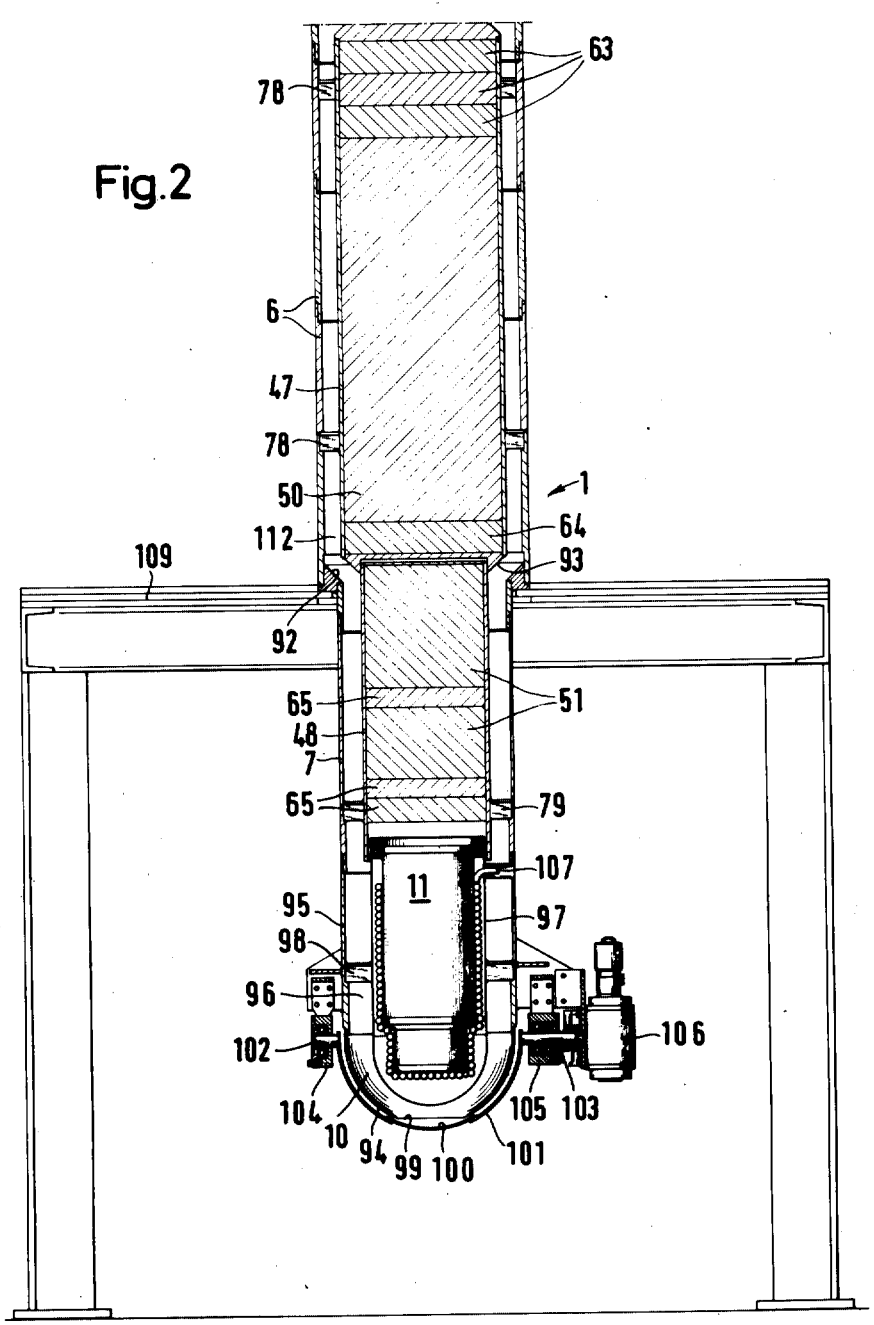

APPARATUS FOR ANALYZING FREE-FLOWING MATERIAL

BACKGROUND OF THE INVENTION

This invention relates to an apparatus for monitoring the condition of bulk or flowable material.

It is desirable from the point of view of economic and environmental protection to repeatedly use, for example, molding sand rather than storing it in waste dumps after a single use. Before reuse, however, the used sand has to be regenerated, that is, it has to be cleaned to remove old bentonite contents. The quality of regeneration has to be continuously monitored to ensure that the cleaning process follows an optimum course. By adding fresh bentonite the regenerated sand regains its form-retaining properties.

The essential component of bentonite is montmorillonite — $Al_2(Si_4O_{10})(OH)_2 nH_2O$ — which excels by its particularly superior swelling properties and dispersibility. The aluminum contents (approximately 10%) permits the monitoring of the progress of the regeneration process by means of an aluminum anaylsis. Expediently, approximately every 15 minutes an analysis value should be obtained to ensure that the analyzing process has an at least quasi-continuous course. Further, the sample taken has to be sufficiently representative (several kg per measurement) in order to maintain sampling errors at a small value. The concentration range of interest is between 1 and 10% bentonite (corresponding to 0.1 and 1% aluminum). The temperature of the sand is above 100° C.

It has not yet been known to utilize the neutron activation analysis with a Cf-252 neutron source for an on-line analyzing process of solid materials in industrial process monitoring. According to this method, concentrations of predetermined components in the flowing material can be determined and the processes can be accordingly controlled. It is an advantage of this method that it can be performed without destruction of the samples and through the walls of tubes that guide the flowing material so that no scooping of samples from the material flow is necessary. Aluminum is well adapted for the process analysis because the radionuclide Al-28 has a short half-life of 2.3 minutes and a relatively high gamma energy of 1.78 MeV.

SUMMARY OF THE INVENTION

It is an object of the invention to provide an apparatus for performing an on-line activation method for monitoring the regeneration of flowable material such as molding sand.

This object and others to become apparent as the specification progresses, are accomplished by the invention, according to which, briefly stated, the apparatus for analyzing material in intermittent sequence comprises a hollow dosing sphere having a predetermined inner volume for forming samples of constant volume of the material introduced thereinto; a hollow radiation sphere connected to the outlet of the hollow dosing shpere; a radiation source supported within and centrally with respect to the hollow radiation sphere for a homogeneous activation of the sample introduced thereinto from the hollow dosing sphere; a hollow measuring sphere connected to the outlet of the hollow radiation sphere; and a detector arranged in the hollow measuring sphere for sensing the activity of the irradiated sample introduced thereinto from the hollow radiation sphere.

Expediently, the hollow dosing sphere, the hollow radiation sphere and the hollow measuring sphere are arranged in a superposed position in such a manner that the molding sand sample is movable by free fall when opening mechanisms are actuated.

It is thus a particular advantage of the invention that an analysis value can be transmitted at least every 5 minutes, that is, in a quasi-continuous manner, thus making possible — based on the analysis values — a direct, immediate control of the regenerating process.

BRIEF DESCRIPTION OF THE DRAWINGS

FIG. 2 is a longitudinal sectional view of a second (lower) part of the same embodiment, adjoining, in axial alignment, the first part shown in FIG. 1.

DESCRIPTION OF THE PREFERRED EMBODIMENT

Figure 1:
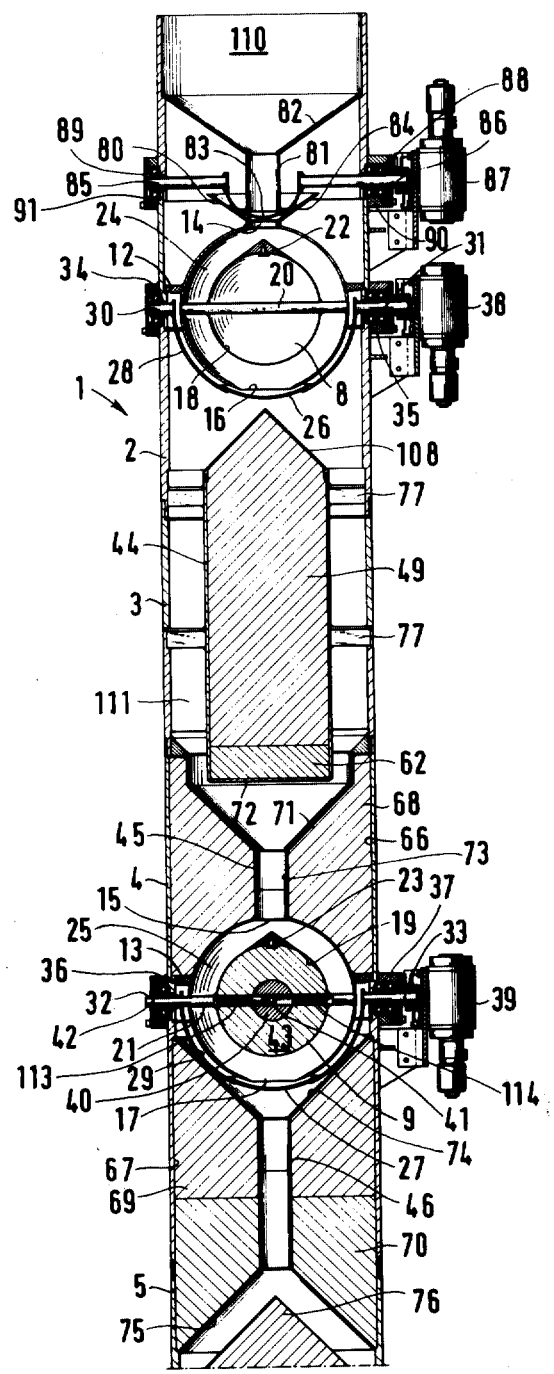
FIG. 1 is a longitudinal sectional view of a first (upper) part of a preferred embodiment of the invention.

Turning now to the Figures, there is illustrated, in longitudinal section, an apparatus for performing an examination of the bentonite contents of molding sand by utilizing the analysis of $Al_2O_3$ by means of neutron activation with Cf-252. For the purpose of simplifying the illustration of the substantially elongated structure, FIGS. 1 and 2 show, respectively, the upper and the lower half of the same apparatus in longitudinal section.

The apparatus generally indicated at 1 comprises axially aligned, serially arranged guide tubes 2, 3, 4, 5, 6 and 7 accommodating spherically shaped hollow bodies 8 and 9 and a generally cylindrical hollow body 10 which has a semi-spherical lower terminal portion. The components 8, 9 and 10, as will be apparent later, successively accommodate the sand sample for dosing, irradiating and measuring, respectively, and accordingly, will be hereafter also referred to as the hollow dosing sphere 8, the hollow radiation sphere 9 and the hollow measuring sphere 10. It is noted that the reason for the cylindrical upper configuration of the measuring sphere 10 is to conformingly accommodate the equally cylindrical detector 11.

The hollow spheres 8 and 9 are each formed of two semi-spherical hollow bodies and are secured by means of rings 12 and 13, respectively, to the inner walls of the respective guide tubes 2 and 4. Each hollow sphere 8 and 9 has an upper and a lower opening 14, 16 and 15, 17, respectively.

In the inside of the hollow spheres 8 and 9 there are centrally positioned respective inner spheres 18 and 19 by means of respective support bars 20 and 21. Aligned with the upper openings 14 and 15, there are arranged respective conical caps 22 and 23 attached to the top of the inner hollow spheres 18 and 19 respectively. The conical caps serve for distributing the sand penetrating through the openings 14 and 15 uniformly in the respective inner volumes 24 and 25 which have identical magnitudes. The lower openings 16 and 17 of the hollow spheres 8 and 9 can be closed and opened by means of spherical segment members 26 and 27, respectively. The spherical segment members are secured to the supports 28 and 29, which, in turn, are carried on rotatable shafts 30, 31 and 32, 33, respectively. The shafts 30–33 are supported on the guide tubes 2 and 4, respectively, by means of ball bearings held in bearing supports 34, 35, and 36, 37, respectively. The shafts 31 and 33 are driven by respective motors 38 and 39.

While the inner hollow sphere 18 of the hollow dosing sphere 8 is empty, the inner sphere 19 of the hollow radiation sphere 9 centrally supports, in an iron core 40, a Cf-252 source 41. The source 41 may be removed, for example, for purposes of repair, by unscrewing it by means of a rod 42 which may be pushed through the shaft 32 and the support 21 for the inner sphere 19. In the inner hollow sphere 19 about the iron core 40 there is disposed $ZrH_2$ in powder form as the inner moderator 43. This additional shield serves for thermalizing the originally fast neutrons in order to suppress the reaction $^{28}Si(n,p)^{28}Al$ which would result in the same radionuclide. The hollow space 25 between the inner and the outer spheres 19 and 9 is, during operation, filled with the sand to be irradiated.

The hollow dosing sphere 8 and the hollow radiation sphere 9 as well as the hollow measuring sphere 10 are arranged above one another in such a manner that the sand, guided by the outer guide tubes 2–7 and inner guide tubes 44, 45, 46, and 47 falls from one sphere to the other; the sand is alternately guided along the center and along the periphery of the tubular structure. The hollow spaces of the guide tubes 44, 47 and 48 which have the shape of axial cylinders contain conformingly shaped graphite members 49, 50 and 51 as well as lead members 62, 63, 64 and 65 for moderating the neutrons and for shielding purposes. The same applies to the intermediate space 66 between the inner guide tube 45 and the outer guide tube 4 and the intermediate space 67 between the inner guide tube 46 and the outer guide tube 5. The intermediate spaces 66 and 67 are filled with graphite parts 68 and 69 and a shaped lead part 70. It is noted that $ZrH_2$ and graphite, respectively, is used because the sand undergoing the regenerating process is hot; otherwise, the use of paraffin or polyethylenes would be more expedient and economical. The inner guide tubes 45 and 46 are formed as the necks of respective funnels 71 and 74, 75. The funnel 71 extends upwardly beyond the closed horizontal portion 72 of the shield 44, 49 and partially surrounds the same. The funnel neck 73 terminates at the upper opening 15 of the hollow radiation sphere 9. The inner guide tube 46 constitutes the neck of two funnels: the upper, downwardly tapering funnel 74 surrounds the lower portion of the hollow radiation sphere 9 and at least the lower outlet opening 17 thereof; whereas the lower, upwardly tapering funnel 75 extends above the upper, conical end 76 of a shield 50. The axial cylinders 44, 47 and 48 are positioned centrally with respect to the outer guide tubes 2–7 by means of spacer ribs 77, 78 and 79.

To the upper opening 14 of the hollow dosing sphere 8 there is welded an outwardly oriented funnel 80. Above the funnel 80 there is positioned the neck 81 of an inlet funnel 82 for guiding the mold sand to be introduced into the apparatus. The outer rim of the inlet funnel 82 is secured to the guide tube 2. The lower end of the neck 81 can be closed or opened by means of a spherical segment 83 which is attached by a support 84 to shafts 85 and 86 supported by bearings 88 and 89 which, in turn, are held in bearing supports 90 and 91 secured to the guide tube 2. The spherical segment 83 can be pivoted into an open or closed position by a motor 87.

The outer diameter of the guide tube 7 is slightly smaller than that of the guide tubes 2–6 to provide, between the tubes 6 and 7 a taper having oblique surfaces 92 and 93. The detector 11 is centrally positioned in the hollow measuring sphere 10 which has a semispherical lower terminal portion 94 and an upper portion 95 of cylindrical configuration. The volume 96 which surrounds the detector 11 is, nevertheless, of the same dimension as the volume 24 and the volume 25 of the hollow dosing sphere 8 and the hollow radiation sphere 9, respectively. Radially inwardly, the volume 96 is bounded by an inner container 97 which, similarly to the hollow measuring sphere 10, has a partly cylindrical and partly semi-spherical shape. The container 97 is centrally attached to the portions 94 and 95 of the hollow measuring sphere 10 by means of a support 98. The lower hollow semi-spherical portion 94 has an outlet opening 99 which may be closed or opened by means of a spherical segment 100. The latter is attached to the shafts 102 and 103 by means of a support 101. The shafts 102 and 103 are, in turn, supported by bearings held in bearing supports 104 and 105. The spherical segment 100 may be pivoted into an open or closed position by a motor 106.

The above described structure thus provides that between the hollow dosing and radiation spheres as well as between the holow radiation and measuring spheres the shields are so arranged that, first, no radiation may directly enter from the hollow radiation sphere 9 into the hollow dosing sphere 8 or the hollow measuring sphere 10 and, second, the sand sample, in its entirety, can be transferred from the hollow dosing sphere into the hollow radiation sphere and from the latter into the hollow meausuring sphere.

The measuring system itself conventionally comprises a sodium iodide (Tl) detector, a high-voltage unit, a pre-amplifier, an amplifier, a stabilizer, a single-channel analyzer, a counter/timer and a voltage source. The detector 11 is a gamma radiation sensor of robust structure. An externally supplied water cooling system 107 is disposed within the inner container 97 and surrounds the detector 11 for protecting it from high temperatures. The auxiliary electronic equipment (not shown in detail) such as the pre-amplifier and the amplifier serve for amplifying the voltage pulses which are emitted by the detector 11 and which are proportionate to the energy of the gamma radiation emanating from the sample by virtue of its earlier irradiation in the hollow radiation sphere 9. Although in the measured gamma spectrum no further peaks can be seen besides the gamma line of the Al-28 at 1.78 KeV, for the sake of precision the gamma peak of the Al-28 is blocked out which may be effected by means of the single-channel analyzer, not shown in detail. Thereafter, only the activity corresponding to the Al-28 is transmitted to the counter. The stabilizer, which is also not shown, is required for measurements taken through extended periods to compensate for a possible drift in the electronic circuitry. The counter/timer which is also not shown, is started by the control system and terminates the measuring process automatically after the set measuring time has lapsed. The accumulated pulse numbers are displayed and may be recorded by a printer, not shown. The number of pulses is directly proportionate to the Al concentration.

The motors 38, 39, 87 and 106 which serve for the opening and closing of the respective gates 26, 27, 83 and 100 are actuated by a control unit, also not shown. This control unit comprises a counting circuit which operates on line frequency and which is set for the duration of the cycle segments "irradiation" and "dosage/measurement". The control of the gates is effected continuously and automatically.

All oblique surfaces, such as the funnel 82, the conical cap 22, the conical upper end 108 of the axial cylinder 44, the funnel 71, the conical cap 23, the cylinders 74 and 75, the conical upper end 76 of the shield 47 and the slanting surfaces 92 and 93, have an inclination of 45° with respect to the horizontal in order to ensure a flow of the sand. The length of the guide tube assembly formed of the external guide tubes 2–7 is obtained by taking into account the necessary radiation shield at the upper inlet comprising the inlet funnel 82 and at the detector 11, against the neutrons and the gamma radiation from the source 41 supported in the hollow radiation sphere 9. About the guide tube assembly 2–7 and its support frame 109, there is provided an additional radiation shield made of graphite blocks (not shown) having a thickness of approximately 30 cm, which, at the outside, is closed by paraffin blocks (including boric acid addition) of a thickness of 20 cm. The activated sand itself need not be shielded.

In the description that follows, the mode of operation of the dosing, irradiating and measuring process performed with the aid of the above-discussed apparatus will be set forth.

First, a representative sample quantity is set to a constant volume in the hollow dosing sphere 8. After closing the storage container 110 which is charged by deflecting one part of the sand from the main production (regeneration) flow, more particularly after closing the neck 81 by the gate 83 and opening the gate 26, the sand sample proceeds by gravity along the intermediate space 111 and the funnel 71, 45 into the inner space 25 of the radiation sphere 9. The gate 27 of the hollow radiation sphere 9 is closed at this time.

Subsequent to a predetermined period which corresponds to the period of irradiation by the Cf-252 source 41 supported in the hollow radiation sphere 9, the gate 27 opens (which may be effected automatically by control means, not shown), whereby the sample slides through the funnel 74, 46 and the intermediate space 112 along the outside of the tubes 47 and 48 into the hollow measuring sphere 10. The gate 100 of the hollow measuring sphere 10 is closed at this time. Simultaneously, the gate 83 above the hollow dosing sphere 8 again opens and the gate 26 at the outlet of the hollow dosing sphere 8 closes. The measuring system including the detector 11 for sensing the gamma activity of the Al-28 in the previously irradiated sand sample is started after a predeterminable delay has lapsed. After a predetermined period which constitutes the measuring period, the outlet gate 100 of the hollow measuring sphere 10 opens. At the same time, the gate 26 again opens and the gates 83 and 27 close. Because of the small total activity of the sand, the latter can again be introduced into the main sand flow without any danger.

If molding sands of different density are used, the sand is, after measurement in the hollow measuring sphere 10, weighed in a container scale (shown), the gate of which is operated synchronously with the gates 83 and 27. Based on the weight, the density can be corrected by computation. An additional switch serves for interrupting the analyzing cycle. Upon actuation of the additional switch, the gate 83 between the hollow dosing sphere 8 and the storage container 110 closes while all the other gates 26, 27 and 100 open whereby the apparatus 1 will be completely emptied. In case hot molding sand is handled by the apparatus, such shutdown may be necessary should the cooling 107 of the detector 11 break down. The cooling water conduit is thus expediently connected with the cycle interrupter switch to automatically operate the latter.

The radionuclide Cf-252 of the radiation source 41 has a triple encapsulation such as $Cf_2O_3$-cermet. It is, in this form, considered as a clad radioactive material. It is installed by screwing it into the iron core 40 which, together with $ZrH_2$ is welded to the inside of the sphere 19 as the moderator 43. The Cf source 41 which is additionally separated from the environment by means of radiation shields 113 and 114 in the inside of the support bar 21, has an activity of 54 mCi (100 $\mu$g) and emits neutrons and gamma rays. Protection against the neutrons is effected by the paraffin or graphite material whereas protection against the gamma radiation is provided by heavy material such as lead or iron.

During neutron activation of the molding sand there is obtained the radionuclide Al-28 which, in its form used in this environment, is to be considered as an unclad radioactive material. A computation of the activity has shown that the generated activity is negligibly small; it amounts to approximately 0.05 $\mu$Ci immediately subsequent to the termination of the irradiation. The activity of the Al-28 has a decay with a half-life of 2.3 minutes and after 20 minutes it is practically no longer present.

It will be understood that the above description of the present invention is susceptible to various modifications, changes and adaptations, and the same are intended to be comprehended within the meaning and range of equivalents of the appended claims.

What is claimed is:

1. In an apparatus for analyzing flowable material in intermittent sequence; comprising
   a. a hollow dosing sphere having an inlet, an outlet and a predetermined inner volume for forming samples of constant volume of the material introduced into said hollow dosing sphere through its inlet;
   b. a hollow radiation sphere having an inlet operatively connected to the outlet of said hollow dosing sphere and an outlet;
   c. a radiation source supported within and centrally with respect to said hollow radiation sphere for a homogeneous activation of the sample introduced into said hollow radiation sphere from said hollow dosing sphere;
   d. a hollow measuring sphere having an inlet operatively connected to the outlet of said hollow radiation sphere and an outlet;
   e. a detector arranged in said hollow measuring sphere for sensing the activity of the irradiated sample introduced into said hollow measuring sphere from said hollow radiation sphere; and
   f. material guide means for combining said hollow dosing sphere, said hollow radiation sphere and said hollow measuring sphere into a structural unit.

2. An apparatus as defined in claim 1, further comprising a first hollow inner sphere supported concentrically within said hollow dosing sphere and a second hollow inner sphere supported concentrically within said hollow radiation sphere; said second hollow inner sphere accommodating said radiation source; and radiation source means positioned in said second hollow inner sphere.

3. An apparatus as defined in claim 2, further comprising a first conical cap secured externally to the top of said first hollow inner sphere and being aligned with the inlet of said hollow dosing sphere and a second conical cap secured externally to the top of said second hollow inner sphere and being aligned with the inlet of said hollow radiation sphere.

4. An apparatus as defined in claim 2, further comprising an axially hollow support bar securing said second hollow inner sphere to said material guide means; said radiation source being movably positioned within said axially hollow support bar.

5. An apparatus as defined in claim 1, further comprising flow control means supported between said hollow dosing sphere and said hollow radiation sphere and between said hollow radiation sphere and said hollow measuring sphere and at the outlet of said hollow measuring sphere; said spheres being in a superposed arrangement; said material being displaceable by gravity from any of said hollow spheres as a function of the setting of the respective flow control means.

6. An apparatus as defined in claim 5, wherein said flow control means comprise gates each having the shape of a spherical segment and each being arranged to close and to open the respective said outlets; said outlets being positioned, respectively, at the lowest location of said hollow dosing sphere, said hollow radiation sphere and said hollow measuring sphere; further comprising support means for pivotally securing said gates to said material guide means; said support means extending through said material guide means; and means for actuating said support means externally of said material guide means for pivoting said gates.

7. An apparatus as defined in claim 5, wherein said measuring sphere has a spherical configuration solely at its lower portion.

8. An apparatus as defined in claim 5, further comprising a charging funnel supported above and connected to the inlet of said hollow dosing sphere; said charging funnel having a neck portion; and gate means for opening and closing said neck portion for controlling the flow of material through said charging funnel.

9. An apparatus as defined in claim 5, wherein said material guide means comprises a guide tube assembly and means for supporting said hollow spheres vertically spaced from one another within said guide tube assembly.

10. An apparatus as defined in claim 9, further comprising radiation shield means disposed in said guide tube assembly between said hollow dosing sphere and said hollow radiation sphere and between said hollow radiation sphere and said hollow measuring sphere; said radiation shield means being positioned for preventing radiation emanating from said hollow radiation sphere from directly reaching said hollow dosing sphere and said hollow measuring sphere; said radiation shield means being further disposed without impeding the flow of the material in the apparatus.

11. An apparatus as defined in claim 10, wherein said radiation shield means comprises a first cylinder positioned in said guide tube assembly coaxially therewith and spaced from walls of said guide tube assembly, said first cylinder being disposed between said hollow dosing sphere and said hollow radiation sphere and having a conical terminus axially aligned with the outlet of said hollow dosing sphere; a second cylinder positioned in said guide tube assembly coaxially therewith between said first cylinder and said hollow radiation sphere; said second cylinder having means defining a throughgoing axial opening including a funnel-shaped enlargement surrounding a lower portion of said first cylinder; the throughgoing opening of said second cylinder merging into said hollow radiation cylinder; a third cylinder positioned in said guide tube assembly coaxially therewith between said hollow radiation sphere and said hollow measuring sphere, said third cylinder having means defining a throughgoing axial opening having a funnel-like enlarged lower terminus; and a fourth cylinder positioned in said guide tube assembly coaxially therewith and spaced from walls of said guide tube assembly, said fourth cylinder being disposed between said third cylinder and said hollow measuring sphere and having a conical terminus surrounded by the funnel-like terminus of the opening in said third cylinder and being axially aligned with the throughgoing opening in said third cylinder and the outlet of said hollow radiation sphere.

12. An apparatus as defined in claim 9, further comprising a support stand for vertically positioning said guide tube assembly and radiation shield means surrounding said guide tube assembly.

* * * * *